(12) United States Patent
Grace et al.

(10) Patent No.: US 10,610,119 B2
(45) Date of Patent: Apr. 7, 2020

(54) SYSTEMS FOR ASSESSING RISK OF SUDDEN CARDIAC DEATH, AND RELATED METHODS OF USE

(71) Applicant: Electus Medical Inc., Laguna Beach, CA (US)

(72) Inventors: Andrew Grace, Cambridge (GB); Peter Van Der Sluis, Laguna Beach, CA (US)

(*) Notice: Subject to any disclaimer, the term of this patent is extended or adjusted under 35 U.S.C. 154(b) by 463 days.

(21) Appl. No.: 14/908,358

(22) PCT Filed: Jul. 31, 2014

(86) PCT No.: PCT/US2014/049217
§ 371 (c)(1),
(2) Date: Jan. 28, 2016

(87) PCT Pub. No.: WO2015/017688
PCT Pub. Date: Feb. 5, 2015

(65) Prior Publication Data
US 2016/0166168 A1    Jun. 16, 2016

Related U.S. Application Data

(60) Provisional application No. 61/860,854, filed on Jul. 31, 2013.

(51) Int. Cl.
*A61B 5/042* (2006.01)
*A61B 5/00* (2006.01)
(Continued)

(52) U.S. Cl.
CPC ........ *A61B 5/0422* (2013.01); *A61B 5/02007* (2013.01); *A61B 5/029* (2013.01);
(Continued)

(58) Field of Classification Search
CPC .................................................. A61B 5/0422
See application file for complete search history.

(56) References Cited

U.S. PATENT DOCUMENTS

| 5,007,436 A | 4/1991 | Smits |
| 7,706,894 B2 * | 4/2010 | Stewart .............. A61B 18/1492 607/122 |

(Continued)

OTHER PUBLICATIONS

International Search Report and Written Opinion dated Feb. 9, 2015, in corresponding International PCT Application No. PCT/US2014/049217, filed on Jul. 31, 2014 (12 pages).

(Continued)

*Primary Examiner* — Lee S Cohen
(74) *Attorney, Agent, or Firm* — Onello & Mello, LLP

(57) ABSTRACT

A medical device may include a sheath, and an elongate member disposed within a distal portion of the sheath, the elongate member configured to reciprocally move between a sheathed configuration and a deployed configuration. The elongate member may be substantially linear and disposed within the sheath while in the sheathed configuration and extend distally from the sheath in a first direction in the deployed configuration. The elongate member may include a first bend disposed distal to the distal portion of the sheath, the first bend directing the elongate sheath in a second direction that is substantially opposite to the first direction, and a second bend distal to the first bend, the second bend directing the elongate sheath in a third direction substantially transverse to the first and second directions. The elongate member may also include a third bend distal to the second bend, the third bend directing the elongate member in approximately the first direction, and a first elongate portion disposed between the second and third bends. The elongate member may also include a second elongate portion distal to the third bend, and at least one electrode.

20 Claims, 4 Drawing Sheets

(51) Int. Cl.
*A61B 5/04* (2006.01)
*A61M 25/00* (2006.01)
*A61B 5/02* (2006.01)
*A61B 5/029* (2006.01)
*A61B 5/0432* (2006.01)
*A61B 5/0452* (2006.01)
*G06F 19/00* (2018.01)
*A61N 1/05* (2006.01)
*A61M 25/06* (2006.01)

(52) U.S. Cl.
CPC ........ *A61B 5/04012* (2013.01); *A61B 5/0432* (2013.01); *A61B 5/04525* (2013.01); *A61B 5/6852* (2013.01); *A61B 5/6869* (2013.01); *A61B 5/7275* (2013.01); *A61M 25/00* (2013.01); *A61M 25/0041* (2013.01); *G06F 19/00* (2013.01); *A61M 2025/0681* (2013.01); *A61N 1/056* (2013.01)

(56) References Cited

U.S. PATENT DOCUMENTS

| | | |
|---|---|---|
| 2004/0249417 A1 | 12/2004 | Ransbury et al. |
| 2008/0065186 A1 | 3/2008 | Pianca et al. |
| 2010/0228330 A1* | 9/2010 | Bornzin .............. A61N 1/056 607/122 |
| 2012/0209343 A1 | 8/2012 | Efimov et al. |

OTHER PUBLICATIONS

Saumarez et al., "Paced ventricular electrogram fractionation and sudden death in hypertrophic cardiomyopathy and other non-coronary heart diseases", 2000, pp. 11-22, vol. 47, Cardiovascular Research, Elsevier Science B.V. (12 pages).

Grace et al., "Risk management in hypertrophic cardiomyopathy", Feb. 10, 2001, pp. 407 and 408, vol. 357, The Lancet (2 pages).

Papadatos et al., "Slowed conduction and ventricular tachycardia after targeted disruption of the cardiac sodium channel gene Scn5a", Apr. 30, 2002, pp. 6210-6215, vol. 99, No. 9, Proceedings of the National Academy of Sciences (6 pages).

Saumarez et al., "Sudden Death in Noncoronary Heart Disease is Associated With Delayed Paced Ventricular Activation", May 27, 2003, pp. 2595-2600, Circulation, American Heart Association, Inc. (6 pages).

Sen-Chowdhry et al., "Non-invasive risk stratification in hypertrophic cardiomyopathy: don't throw the baby out with the bathwater", Jun. 5, 2008, pp. 1600-1602, vol. 29, European Heart Journal, European Society of Cardiology (3 pages).

Saumarez et al., "Paced ventricular electrogram fractionation predicts sudden cardiac death in hypertrophic cardiomyopathy", Apr. 2, 2008, pp. 1653-1661, vol. 29, European Heart Journal, European Society of Cardiology (9 pages).

* cited by examiner

SYSTEMS FOR ASSESSING RISK OF SUDDEN CARDIAC DEATH, AND RELATED METHODS OF USE

CROSS-REFERENCE TO RELATED APPLICATION APPLICATIONS

This patent application is the U.S. national phase entry under 35 U.S.C. § 371 of International PCT Patent Application No. PCT/US2014/049217, filed Jul. 31, 2014, which claims the benefit of priority under 35 U.S.C. § 119 to U.S. Provisional Patent Application No. 61/860,854, filed Jul. 31, 2013, the entireties of each of which are incorporated herein by reference.

TECHNICAL FIELD

Various embodiments of the present disclosure relate generally to systems for assessing a risk of sudden cardiac death and related methods of use.

BACKGROUND

Sudden cardiac death is a natural death due to cardiac causes. In some cases, sudden cardiac death is caused by ventricular fibrillation and/or ventricular tachycardia. Ventricular fibrillation is a condition in which there is uncoordinated contraction of the cardiac muscle of the ventricles in the heart, making them quiver rather than contract properly. Ventricular fibrillation is a commonly identified arrhythmia in cardiac arrest patients that is often only detectable by electrocardiography. Ventricular tachycardia is a tachycardia, or fast heart rhythm, that originates in one of the ventricles of the heart.

An implantable cardioverter-defibrillator (ICD) is a small battery-powered electrical impulse generator that is implanted in patients who are at risk of sudden cardiac death due to ventricular fibrillation and/or ventricular tachycardia. An ICD is programmed to detect cardiac arrhythmia and correct it by delivering a jolt of electricity. Implanting an ICD is similar to implanting a pacemaker. Similar to pacemakers, ICDs typically include electrode wire(s) that pass through a vein to the right chambers of the heart, usually lodging in the apex of the right ventricle.

While ICD insertion is a safe and routine procedure, as with any surgical procedure, there is a risk for complications. The range of complications for ICDs is extensive as problems can frequently emerge with the electrode wires. Further, ICDs may be relatively expensive. There are currently no reliable predictors of sudden cardiac death to identify the best candidates for ICD implantation.

Thus, there remains a need for improved systems for assessing a risk of sudden cardiac death.

SUMMARY OF THE DISCLOSURE

In one aspect of the disclosure, a medical device may include a sheath, and an elongate member disposed within a distal portion of the sheath, the elongate member configured to reciprocally move between a sheathed configuration and a deployed configuration. The elongate member may be substantially linear and disposed within the sheath while in the sheathed configuration and extend distally from the sheath in a first direction in the deployed configuration. The elongate member may include a first bend disposed distal to the distal portion of the sheath, the first bend directing the elongate sheath in a second direction that is substantially opposite to the first direction, and a second bend distal to the first bend, the second bend directing the elongate sheath in a third direction substantially transverse to the first and second directions. The elongate member may also include a third bend distal to the second bend, the third bend directing the elongate member in approximately the first direction, and a first elongate portion disposed between the second and third bends. The elongate member may also include a second elongate portion distal to the third bend, and at least one electrode.

Various embodiments of the disclosure may also include one or more of the following aspects: wherein each of the first bend, the second bend, and the third bend is a pre-shaped bend in the elongate member, and the elongate member assumes the pre-shaped bends in the absence of an applied force; wherein the at least one electrode includes a first electrode disposed along the first elongate portion, a second electrode disposed at the third bend, a third electrode disposed on the second elongate portion, and a fourth electrode disposed on the second elongate portion downstream of the third electrode; wherein the first bend is configured to extend through the tricuspid valve and into the right ventricle of a patient; wherein the first elongate portion is configured to substantially conform to an inner surface of the right ventricle along an inferior wall to the apex; wherein the third bend is configured to be located at approximately the apex of the heart; wherein the second elongate portion is configured to substantially conform to the septal wall of the heart; and further including a distalmost tip configured to be disposed in the right ventricle outflow tract of the patient.

In another aspect of the disclosure, a method for determining a risk of sudden cardiac death within a patient may include receiving data including at least one electrogram generated from the patient, and analyzing the data to determine a risk of the patient for sudden cardiac death. The method may also include generating an indicia of the determined risk of sudden cardiac death, and transmitting the indicia to a user.

Various embodiments of the disclosure may also include one or more of the following aspects: wherein the received data is collected by at least one electrode disposed in the cardiovascular system of the patient; wherein the at least one electrode includes a first electrode contacting an inferior wall of a right ventricle, a second electrode contacting a wall of the right ventricle proximate to the apex, and a third electrode contacting a septal wall of the right ventricle; wherein the at least one electrogram includes a plurality of electrograms generated from a plurality of electrodes within the cardiovascular system of the patient; wherein analyzing the data includes comparing the at least one electrogram to a database of electrograms; wherein a fractionation of the at least one electrogram is compared to a fractionation in the database of electrograms; wherein the fractionation is indicative of discontinuous conduction through the heart muscle of the patient; wherein generating an indicia of the determined risk of sudden cardiac death is based on age, gender, symptoms, drug use, electrocardiograms, status of the coronary arteries, images of coronary arteries, or ejection fraction of the patient; and wherein the indicia includes a score indicating a signal delay.

In yet another aspect of the disclosure a system for determining a risk of sudden cardiac death within a patient may include a data storage device, and a processor configured to execute instructions to perform a method. The method may include receiving data including at least one electrogram generated from the patient; and analyzing the data to determine a risk of the patient for sudden cardiac death. The method may also include generating an indicia of the determined risk of sudden cardiac death.

Various embodiments of the disclosure may also include one or more of the following aspects: further including an elongate member having a plurality of electrodes.

BRIEF DESCRIPTION OF THE FIGURES

The accompanying drawings, which are incorporated in and constitute a part of this specification, illustrate various exemplary embodiments and together with the description, serve to explain the principles of the disclosed embodiments.

DETAILED DESCRIPTION

Reference will now be made in detail to embodiments of the present disclosure, examples of which are illustrated in the accompanying drawings. Wherever possible, the same reference numbers will be used throughout the drawings to refer to the same or like parts.

Figure 1:
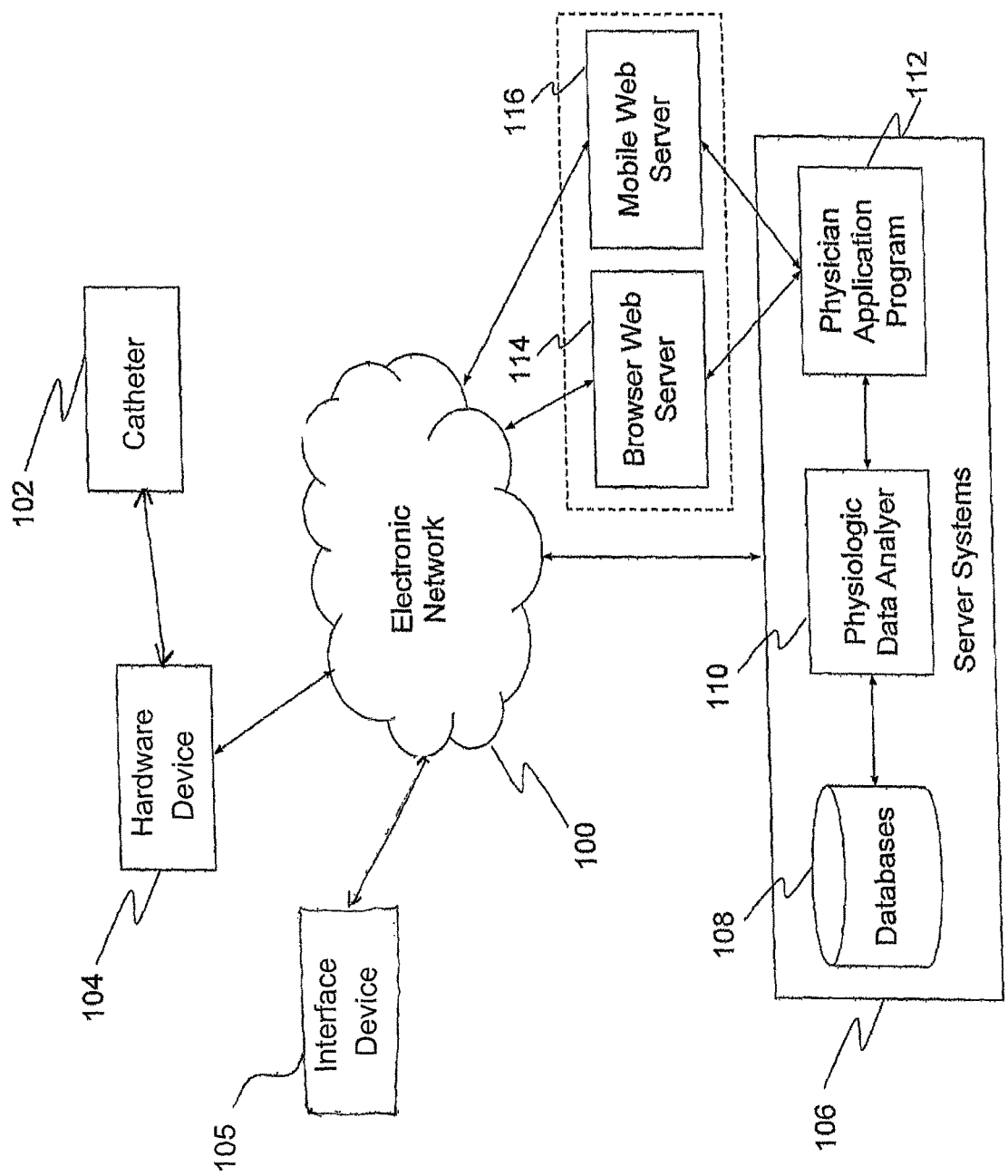
FIG. 1 is a schematic view illustration of a system in accordance with an embodiment of the present disclosure.

Referring now to the enclosed figures, FIG. 1 is a schematic diagram of a system and environment for collecting, processing, and displaying sudden cardiac death risk data, according to an exemplary embodiment of the present disclosure. As shown in FIG. 1, the system and environment may include a plurality of catheters 102, hardware devices 104, and interface devices 105 disposed in communication with an electronic network 100. FIG. 1 depicts one of each of catheter 102, hardware device 104, and interface device 105. It is understood, however, that any number of catheters 102 and associated hardware devices 104 and interface devices 105 may be used in the system. The catheters 102, hardware devices 104, and interface devices 105 comprise the portions of the system that the physician or other health care provider interacts with. This disclosure first describes these aspects of the system, followed by disclosure of the remainder of the system, including the servers, and exemplary methods of use.

Catheter 102

Figure 2:
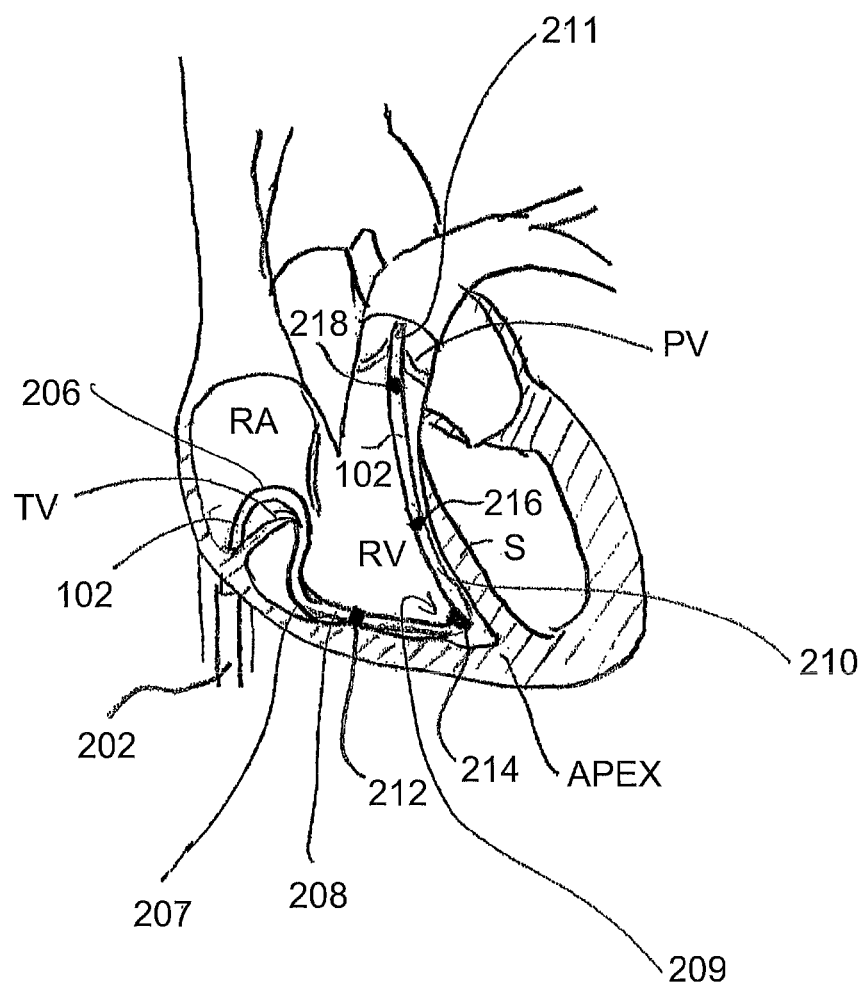
FIG. 2 is an in vivo illustration of a catheter in accordance with an embodiment of the present disclosure.

Catheter 102 and hardware device 104 are configured to gather the data that will be used to predict the risk of sudden cardiac death and/or the need for an ICD. As shown in FIG. 2, catheter 102 may configured to be inserted into the cardiovascular system, e.g., the heart, of a patient. In some embodiments, catheter 102 may be inserted into the patient by a physician, e.g., a cardiologist, or another suitable person. In some embodiments, the cardiologist may utilize catheter 102 during a patient visit where a coronary angiogram is being performed. In some embodiments, the patient may only need to be sedated for approximately an additional 15 minutes, although other sedation times are also contemplated. Thus, the patient may experience minimal discomfort. Catheter 102 may be disposed within a sheath 202 or other like overtube. Sheath 202 may be any conventional sheath that can be inserted at least partially into a body lumen. Sheath 202 may be flexible, or include a portion that is flexible, to allow sheath 202 to be maneuvered within the body lumen, such as, e.g., portions of the cardiovascular system. In one embodiment, sheath 202 may be inserted through a vein in the groin or leg and directed into the heart of a patient. In addition, other conventional techniques of guiding and positioning sheath 202, including guidewires and/or imaging techniques, can be used to guide sheath 202 and catheter 102 into position.

Catheter 102 may be configured to have a geometry that assists in navigating the tortuous pathways of the cardiovascular system leading to the right atrium RA and the right ventricle RV. In one embodiment, catheter 102 may be formed of a shape memory material, such as, e.g., Nitinol, or any other suitable material. Once the distal end of sheath 202 reaches the entrance of the right atrium RA just proximal to the inferior vena cava, catheter 102 may extend distally from the distal end of sheath 202 and have a pre-shaped set of bends to follow a path within the right ventricle RV, such as the path shown in FIG. 2. Prior to catheter 102 exiting sheath 202, sheath 202 restrains the shape of catheter 102 to a substantially linear shape. Upon exiting sheath 202, however, catheter 102 has a set of discrete bends and curves to extend from the right atrium RA, through the tricuspid valve TV, into the right ventricle RV, conform to surfaces of the right ventricle RV, and exit the right ventricle RV at the pulmonary valve PV. More particularly, a bend 206 of catheter 102 may be U-shaped and extend from just distal sheath 202, through the tricuspid valve TV, and into the right ventricle RV. U-shaped bend 206 may direct catheter 102 approximately 180° from the inferior vena cava, through the right atrium RA and tricuspid valve TV to the right ventricle RV. Catheter 102 may extend from U-shaped bend 206 to another bend/curve 207 that directs catheter 102 toward the inner surface of the right ventricle RV near the tricuspid valve TV. Bend 207 may direct catheter 102 toward a catheter portion 208 that substantially conforms to the inner surface of the right ventricle RV along the inferior wall to the apex. Catheter portion 208 may terminate at a bend 209 located approximately at the apex, which directs catheter 102 toward the pulmonary valve PV via a catheter portion 210. Catheter portion 210 may substantially conform to the septal wall and extend toward a distal tip 211 of catheter 102. Distal tip 211 of catheter 102 may terminate in or around the right ventricle outflow tract at the pulmonary valve PV or within the pulmonary artery. This overall catheter configuration, including the correspondence between various bends/catheter positions, and right ventricle geometry may provide stability to catheter 102 and to minimize movement. They may also provide reference locations for clinicians so that locations of the various electrodes (described below) are standardized and facilitate data collection that is robust and comparable between different patients and different patient groups.

Catheter 102 may include a plurality of electrodes, for example three to ten, or another suitable number of electrodes. The electrodes may provide stimulation pulses to the heart tissue, measure the tissue response, and send the response along the catheter 102 back to a hardware device 104. Each electrode may be a pair of electrodes and may be bipolar electrodes, although other configurations, such as, e.g., monopolar electrodes are also contemplated. In some embodiments, electrodes may be irregularly spaced about catheter 102, although other configurations, including regular spacing, are also contemplated. In one exemplary embodiment, catheter 102 may include eight bipolar sets of electrodes, although other numbers of electrodes are also contemplated.

In another embodiment, catheter 102 may include a first electrode 212 that is configured to be deployed along the inferior wall of right ventricle RV between the tricuspid valve TV and the apex (e.g., along catheter portion 208), and a second electrode 214 configured to be deployed along the inner surface of right ventricle RV proximate the apex (e.g., at bend 209). A third electrode 216 may be deployed along the septal wall of right ventricle RV between the apex and the pulmonary valve PV (e.g., along catheter portion 210), and a fourth electrode 218 may be deployed along the outflow tract of right ventricle RV proximate (just proximal to) the pulmonary valve PV (e.g., distal to third electrode 216 along a part of catheter portion 210). Each electrode may be a cylindrical electrode that extends around the circumference of the catheter 102, although other electrode configurations are also contemplated. In some embodiments, electrode placement may be configured to subtend as much of the ventricular myocardium as possible. The septal placement of electrodes may allow access to the left ventricle that is otherwise difficult to access for electrophysiological recording. In some embodiments, the arrangement of electrodes may provide data from the septum. Electrodes may be disposed in the outflow tract as this is some distance from other parts and has particular and interesting electrical properties. For similar reason, an electrode may be placed on the inferior wall 212 and at the apex 214. Electrode placement may be configured to obtain maximum coverage of muscle.

In some embodiments, catheter 102 may be configured for single (e.g., one-time, disposable, etc.) use, while in other embodiments, catheter 102 may be configured to be used multiple times. Catheter 102 may have any suitable size and may include a central lumen for a guidewire. In one exemplary embodiment, catheter 102 may have a 7 French diameter, although other suitable diameters and configurations are also contemplated.

Hardware Device 104

In one embodiment, a hardware device 104 may be coupled to a proximal end of a catheter 102 to control the stimulation pulsing and data acquisition by the electrodes. In some embodiments, hardware device 104 may deliver stimuli to a patient's heart and obtain data. Hardware device 104 may include a memory, a battery (or other suitable element for powering device 104), and/or a transceiver. Each of hardware devices 104 may be connected to electronic network 100 through a cellular network and/or a Wi-Fi network. Thus, each of hardware devices 104 may be configured to collect physiological data from a patient via catheter 102, and transmit collected physiological data over electronic network 100. Each of hardware devices 104 may also have a web browser or mobile browser installed for receiving and displaying content from web servers, in addition to other components to facilitate with operation, such as, e.g., start and stop buttons, keyboards, touch screens, and the like. Electronic network 100 may be the Internet, or any other combination of wired and/or wireless electronic networks.

Figure 3:
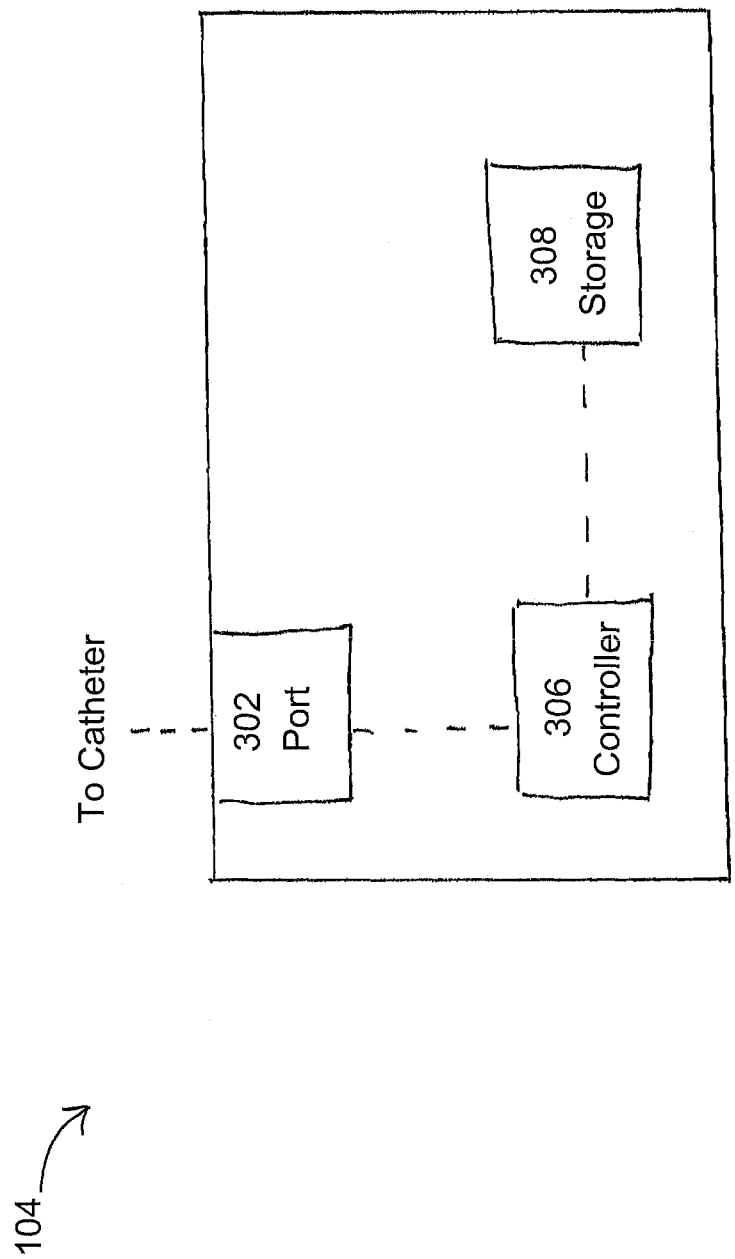
FIG. 3 is a schematic view illustration of a hardware device in accordance with an embodiment of the present disclosure.

As seen in FIG. 3, hardware device 104 may include a port 302 for coupling a proximal end of catheter 102 (referring to FIG. 2) to hardware device 104. Hardware device 104 may include a controller 306. Controller 306 may include one or more processors coupled to one or more non-transitory computer readable storage devices 308 that may perform any of the actions described herein for operating catheter 102, storing collected data, and transmitting data to server system 106 (to be described herein) via electronic network 100. Hardware device 104 may be configured to allow a user to log into a doctor or hospital account and create patient profiles. Hardware device 104 may be configured to perform patient testing while offline or online, if desired. Hardware device 104 may include or be coupled to a visual display to assist a user during operation of hardware device 104. In some embodiments, hardware device 104 may be configured to show a progress of the data collection, indicate that data collection is complete, and/or indicate that transmission to server system(s) 106 is complete. In some embodiments, hardware device 104 may include error logs and solutions. In some embodiments, hardware device 104 may use error logs to alert the physician and other members of the clinical team to a problem. An error may indicate that a relocation of catheter 102 positioning is desired to obtain optimal data. An error may also indicate that, during the course of the study, the clinical condition of the patient has changed and the device may provide further alerts to the medical team of this occurrence for, e.g., remedial action by the medical team. In addition, a failsafe position may be adopted if the patient's condition changes so that the test procedure is automatically terminated. After such a termination, the already collected data may be safely stored for appropriate analysis, including, e.g., its relationship to the patient's condition. In some embodiments, hardware device 104 may be in a 120 volt, 60 Hz configuration, while in other embodiments, hardware device 104 may be in a 240 volt 50 Hz configuration, although other suitable configurations are also contemplated.

Controller 306 may be configured to run a plurality of algorithms to prepare and control catheter 102 for data collection. In one embodiment, controller 106 may cause one of the plurality of electrodes to pulse at a given time (for example, via square wave pulses), and cause the remaining plurality of electrodes to record data, such as, e.g., the electric heart wall response at the various locations of the remaining plurality of electrodes. The electrograms thereby recorded may vary by location within the ventricle related to the specific nature of the heart tissue in that location, but also related to the contact with the tissue that is made. The amplitude, duration, morphology and number of components of the individual electrograms may be analyzed through the systems described. These may vary in response to the timing of the pulses, and the relationships between the characteristics of the electrograms recorded at different times will be measured and compared. For example, in the embodiment described in FIG. 2, first electrode 212 may pulse, while second, third, and fourth electrodes 214, 216, and 218 may record data. Controller 306 may select the first electrode to pulse based on which electrode initially provides the strongest signal or based on another suitable method. Each of first, second, third, and fourth electrodes 212, 214, 216, and 218 may rotate between a pulsing or recording mode, where no more than one of electrodes 212, 214, 216, and 218 act as a pulsing electrode at a given time.

During data collection, controller 306 may send pulses in a delayed fashion. For example, pulses may be first sent with a delay of 450 milliseconds between pulses or in relation to the recording and inscription of previous intrinsically generated electrograms. Controller 306 may be further configured to send pulses with a decremental or even an incremental delay. For example, subsequent pulse delays may be, e.g., two milliseconds shorter or two milliseconds longer than a previous delay. Thus, if a first delay between pulses is 450 milliseconds, a subsequent delay may be 448 milliseconds. The purpose of the decremental/incremental delays is to fully and dynamically interrogate the heart muscle and observe the response of the tissue to the conditions that may trigger an arrhythmia and potentially trigger an episode of sudden cardiac death. The particular pulsing sequence may be optimized based upon clinical trials, and may be subject to modification based upon future clinical trials, if desired. A goal of the pulsing sequence is to extract data as quickly as possible. The data collected by hardware device 104 may be filtered by conventional mechanisms to prepare the extracted data for sending through the electronic network 100.

In some embodiments, hardware device 104 may be compatible with standardized equipment at cardiology centers, hospitals, or the like. Hardware device 104 may be fitted with ports and connections to allow compatibility with a variety of currently used standard electrophysiological, cardiological, radiological and other medical and non-medical devices. In some embodiments, hardware device 104 may be customized to a specific country or environment in which hardware device 104 will be used, as well as being compatible with the equipment that a given cardiology center currently uses.

In some embodiments, hardware device 104 may implement appropriate security protocols, such as requiring the physician to enter logon credentials, so as to appropriately limit access to patient data and comply with regulations, such as the Health Insurance Portability and Accountability Act (HIPAA).

Interface Device 105

In one embodiment, each of the interface devices 105 may include a server, personal computer, tablet computer, mobile device, smartphone, and/or personal digital assistant ("PDA") disposed in communication with electronic network 100. For example, in one embodiment, each of interface devices 105 may be a touchscreen enabled device, such as an Apple iPad, Samsung Galaxy, Amazon Kindle, Microsoft Surface, or any other equivalent or similar device. Each of interface devices 105 may have a web browser or mobile browser installed for receiving and displaying content from web servers. Thus, each of the interface devices 105 may be configured to receive and display data that is received and processed from hardware devices 104, over electronic network 100. For example, interface device 105 may receive output from the electronic network and display it to the user. The output may include a prediction of a risk of death due to a sudden cardiac event. The output may be a low, medium, or high prediction.

In some embodiments, interface device 104 may implement appropriate security protocols, such as requiring the physician to enter logon credentials, so as to appropriately limit access to patient data and comply with regulations, such as the Health Insurance Portability and Accountability Act (HIPAA).

Server Systems

As shown in FIG. 1, a plurality of server systems 106, a browser web server 114, and/or a mobile web server 116 may also be disposed in communication with electronic network 100. In one embodiment, server systems 106 may be configured to receive physiological data from hardware devices 104 over electronic network 100. Any of the devices or functionality of server systems 106, browser web server 114, and/or a mobile web server 116 may be combined together or separated, and may be operated by a single administrative entity, or outsourced to one or more other entities, such as a web hosting entity, web storage entity, and/or cloud computing service.

As shown in the embodiment of FIG. 1, server systems 106 may include a data analyzer 110, which may analyze the received physiological data. Specifically, data analyzer 110 may be configured to analyze received physiological data for assessing a patient's risk for sudden cardiac death, and/or perform any other analysis, classification, and/or sorting of detected sudden cardiac death risk factors and/or patients having sudden cardiac death risk factors, as will be described in more detail below.

Server systems 106 may also include one or more databases 108, where data analyzer 110 may be configured to store the received physiological data and/or the computed data. Any received data may be stored in the databases 108 in an encrypted form to increase security of the data against unauthorized access.

Server systems 106 may also include a health-care provider application program 112 that allows a physician or other health care provider to control parameters of the system, such as values used by the data analyzer 110 in the analysis. The application program 112 also displays data to the physician and allows the physician to select types of data to display, time periods of the data to display, levels of data detail to display and other operating parameters of the system. In response to a query by the physician, the application program 112 may fetch and display data from the databases 108. The application program 112 may implement appropriate security protocols, such as requiring the physician to enter logon credentials, so as to appropriately limit access to patient data and comply with regulations, such as the Health Insurance Portability and Accountability Act (HIPAA). In some embodiments, server system 106 may track and bill procedures and/or diagnosis to accounts associated with the physician, patient, hospital, or other entity. Server system 106 may also be configured to generate reports based upon numerous criteria, such as, e.g., patient account, region, zip code, territory, country, continent or the like.

As shown in FIG. 1, server systems 106 may be disposed in communication with a browser web server 114 and/or a mobile web server 116. Each of browser web server 114 and/or mobile web server 116 may be configured to interact with interface devices 105, such as to generate appropriate displays to facilitate user interaction with the application program 112. For example, browser web server 114 and/or mobile web server 116 may be configured to generate a window-metaphor based computer user interface on a screen of interface devices 105 or screen (not shown) coupled to the remote server systems 106, or the browser web server 114 and/or mobile web server 116 may generate web pages that are rendered by a browser or application of the interface devices 105. The interface devices 105 and the browser web server 114 and/or mobile web server 116 may communicate with each other using an appropriate encrypted protocol, such as Hypertext Transfer Protocol Secure (HTTPS).

Exemplary Method

Figure 4:
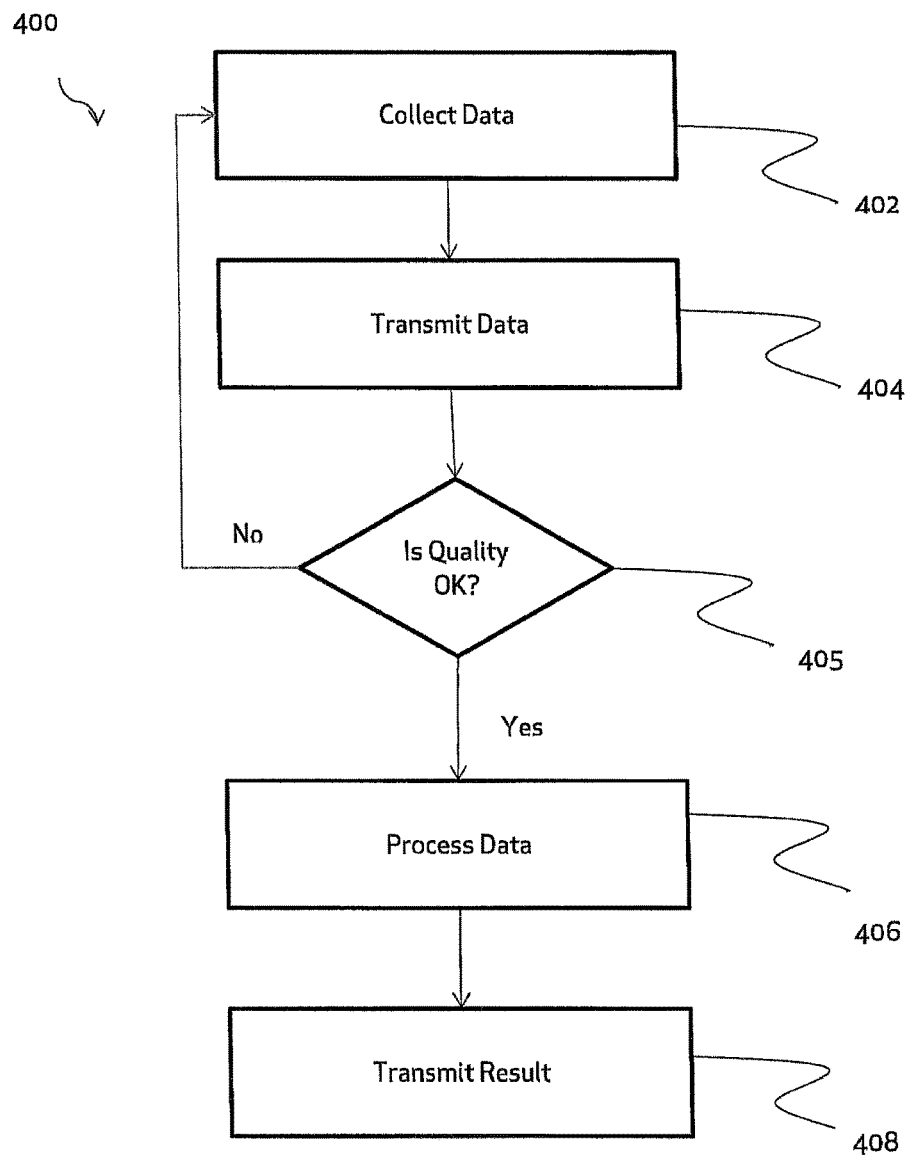
FIG. 4 is a flowchart of an exemplary method in accordance with an embodiment of the present disclosure.

FIG. 4 is a flow diagram of a method 400 for collecting, processing, and displaying sudden cardiac death data, e.g., using the exemplary system and devices of FIGS. 1-3, according to an exemplary embodiment of the present disclosure. As shown in FIG. 4, method 400 may initially include collecting sudden cardiac death data from one or more patients (step 402). For example, a physician may locate a catheter 102 within a patient and run a test algorithm on the electrodes via hardware device 104. After hardware device 104 sends the required stimulation pulses and collects the required data, server system(s) 106 may receive sudden cardiac death data from hardware device 104, which may then be stored in database(s) 108 (step 404). The data may be collected in response to a preset protocol of decremental/ incremental stimulation. The exact protocol may vary and be simplified with fewer pulses, or made more complex with more pulses based on the results of further clinical experience and clinical trials. The complete dataset of electrograms and other recorded information may be sent to the cloud for subsequent analysis.

Method 400 then may include checking that the transmitted data is of sufficient quality (step 405). A human analyst or a computer program may analyze data received from hardware device 104 to ensure that the data is of sufficient quality to analyze. The main limiting factor in the quality of the data would be if insufficient electrodes had been able to record data. In some embodiments, at least two electrodes may be required to collect sufficient data. A complete data set may include an electrogram from all electrodes at numerous pulsing intervals. The analyst or computer may also reject data if the noise level within the data is too high. If the data is rejected, a signal may be sent to, e.g., hardware device 104 or interface device 105, indicating that the sample quality is poor and that data must be recollected at step 402 before any analysis may be conducted. It is contemplated that step 405 may be fully automated and performed without a human analyst.

If at step 405, the transmitted data is determined to be of sufficient quality, the sudden cardiac death data may be processed by data analyzer 110 to assess a risk for sudden cardiac death. The analyst may, after conducting a quality check of the data checking for completeness and noise, direct the signals to be entered into the next stage of analysis. The analysis may include an automatic assessment of the components of the individual electrograms, including, e.g., the number of components, the timing of each of these components in regard to the timing of the pulse (which is the extent to which they are delayed). In some embodiments, the collected data may be compared to animal models and/or patient models showing the characteristics of the delay and fractionation (the breakup of the electrogram into multiple components) that has been associated with possession of damaging underlying muscle on the background of the possession of an adverse genetic variant or some acquired condition or indeed a combination of genetic and acquired heart conditions. In other words, collected data may be processed before a patient's risk for sudden cardiac death is calculated.

Data analyzer 110 may analyze electrograms generated based on data collected by catheter 102 and hardware device 104. For example, the electrograms produced by diseased muscle in a patient deemed to be at risk will take a different shape than the electrograms produced by muscle observed in a low risk cardiac patient. In some embodiments, data analyzer 110 may search for fractionation within the received electrograms. The fractionation patterns may have been associated in both animal models of arrhythmias with the characteristics of sudden death conditions and patients already seen to be at high risk as being associated with risk and a predisposition to sudden death.

In some embodiments, electrograms taken from patients deemed to be at high risk may have more components with delays, and this is described as having a fractionated pattern. Fractionation has been associated with diseased tissue and may represent discontinuous conduction through the muscle that may have arisen either through the presence of structural change, e.g., due to scar, or alternatively through some functional change due to the presence of genetic variants in proteins involved in the normal transmission of the cardiac impulse. These proteins may often be ion channels but could be other proteins. The pattern of delay may also be modified with other changes in the electrical properties of the heart, and the pattern of the electrograms may additionally reflect all these changes. The characteristics observed and measured in the electrograms may include size (amplitude), numbers of components, and delay in each of the components. The data may be converted to a format that is quantitative and summarizes the conduction through the ventricular muscle.

Analyzer 104 may interrogate each individual electrogram. In some embodiments, several thousand electrograms may be recorded during the course of study of a single patient, or another suitable number of electrograms may be recorded, if desired. The electrogram may be categorized by the timing of its collection in the decremental/incremental protocol and all characteristics of the electrogram may be related to that timing. Specific measurements may be made automatically that describe the numbers of components of the electrogram, their amplitude and their timing related to the delivered pulse. These measurements may be open to manual and visual checking by an expert human analyst. The final output may be a description of the composite of timing and degree of breakup of the signal and this may use an averaging method and/or may be adapted based on prospective clinical experience. In some embodiments, the output of the signals that have been observed in animal models and human patients may be compared to the individual patient under study. Those patients at higher risk deviate incrementally from the results obtained in a gold standard normal population that will be newly acquired. In some embodiments, a score may be reported in milliseconds representing a delay. A higher delay may correspond to a higher risk of sudden cardiac death. The results may be presented to the physician as a continuous rather than a categorical variable, and the physician may use the information in conjunction with other data they have available from the patient to make a diagnosis and/or treatment recommendation. In some embodiments, categorical recommendations may be made with the caveat that other data would also be needed by the physician as would be usual practice with any single items of clinical data obtained from patients.

In some embodiments, a database of collected data may be generated. The predictive capability of the database may increase as the database grows. That is, as the diseases that various patients have may be divergent, their responses to disease may be heterogeneous, and the procedure results that are accumulated may reflect that and have the individual signature of that patient with that disease with past histories and outcomes. This may allow prospective prediction in new patients as they then present. Data analyzer 110 may also process any number of additional characteristics relevant to assessing a patient's risk of sudden cardiac death, including, but not limited to age, gender, symptoms, drug use, electrocardiograms, status of coronary arteries, images of coronary arteries, ejection fraction, among others. Additional data may be input to data analyzer 110 via hardware device 104, interface device 106, or via another input mechanism, such as, e.g., a hospital input terminal or a patient database entry website that communicates with data analyzer 110 via electronic network 100.

The prediction of sudden death may reflect general heart function and most specifically the function of the left ventricle chamber may be used. In some embodiments, data analyzer 110 may weigh such factors according to a given factor's relative significance in determining a risk of sudden cardiac death. In some embodiments, data analyzer 110 may ignore data if it is deemed to be anomalous but the physician skilled in the art is likely to be aware that on occasion such anomalies may occur. In some embodiments, the risk assessment may be performed after the data collection procedure at step 402. In some embodiments, the risk assessment may be generated while hardware device 104 and catheter 102 are offline, e.g., in approximately 48 hours, although other suitable time frames are also contemplated. In some embodiments, data analyzer 110 may analyze data from catheter 102 and hardware device 104 in real-time. That is, at the conclusion of a data collection procedure at step 402, the physician may utilize interface device 105 or hardware device 104 to visualize a risk assessment determined by data analyzer 110. In some embodiments, the physician may be directed to recollect data at step 402, e.g., if the data was determined by the analyst or data analyzer 110 to be anomalous. In other embodiments, the physician may view the risk assessment and choose to recollect data at step 402 even if the analyst or data analyzer 110 does not transmit specific instructions to recollect data.

From step 406, method 400 may proceed to step 408, where data analyzer 110 may transmit an assessment of a patient's risk of sudden cardiac death to interface device 105, where the assessment may be accessed by a user, such as, e.g., the patient's cardiologist. In one embodiment, data analyzer 110 may transmit a risk level of sudden cardiac death, such as, e.g., low, medium, or high, if desired. Each risk level may be associated with a value range calculated at step 406.

It will be apparent to those skilled in the art that various modifications and variations can be made in the disclosed systems and processes without departing from the scope of the invention. Other embodiments of the invention will be apparent to those skilled in the art from consideration of the specification and practice of the invention disclosed herein. It is intended that the specification and examples be considered as exemplary only. The following disclosure identifies some other exemplary embodiments.

We claim:

1. A medical device, comprising:
    an elongate member having a pre-shaped set of bends configured to follow a path of a right ventricle (RV) of a heart, the elongate member configured to take a substantially linear shape within a sheath and reciprocally move between a sheathed configuration and a deployed configuration extending distally from the sheath in a first direction, wherein the elongate member in the deployed configuration includes:
        a U-shaped first bend directing the elongate member in a second direction that is substantially opposite to the first direction, the first bend configured to bend through the tricuspid valve of the heart when disposed in the RV;
        a second bend directing the elongate member in a third direction substantially transverse to the first and second directions, the second bend configured to direct the elongate member along an inferior wall to an apex of the RV; and
        a third bend directing the elongate member in a fourth direction, the third bend configured to direct the elongate member from the apex toward a pulmonary valve of the heart; and
    at least one electrode disposed on or in the elongate member and configured to interrogate the heart muscle and observe a tissue response.

2. The medical device of claim 1, wherein each of the first bend, the second bend, and the third bend is a pre-shaped bend in the elongate member, and the elongate member assumes the pre-shaped bends in the absence of an applied force.

3. The medical device of claim 1, wherein the at least one electrode includes a first electrode disposed along a first elongate portion of the elongate member, a second electrode disposed at the third bend, a third electrode disposed on a second elongate portion of the elongate member, and a fourth electrode disposed on the second elongate portion downstream of the third electrode.

4. The medical device of claim 1, wherein the elongate member includes a first elongate portion extending from the second bend to the third bend.

5. The medical device of claim 4, wherein the elongate member further includes a second elongate portion extending from the third bend.

6. The device of claim 5, wherein the second elongate portion is configured to substantially conform to the septal wall of the heart.

7. The device of claim 6, wherein the second elongate portion includes one or more electrodes.

8. The device of claim 4, wherein the first elongate portion is configured to substantially conform to an inner surface of the right ventricle of the heart.

9. The device of claim 8, wherein the first elongate portion includes one or more electrodes.

10. The medical device of claim 1, wherein the elongate member comprises a distalmost tip configured to be disposed in the right ventricle outflow tract of the heart.

11. The device of claim 1, wherein the at least one electrode includes a plurality of electrodes, including a pulse electrode and at least one recording electrode.

12. The device of claim 1, wherein the at least one electrode includes a plurality of electrodes operatively controlled by a controller configured to selectively rotate one or more of the plurality of electrodes between a pulsing mode and a recording mode.

13. The device of claim 1, wherein the elongate member forms a distal end of a catheter extending through the sheath.

14. The device of claim 13, wherein the at least one electrode includes a plurality of electrodes configured to provide stimulation pulses to tissue of the heart, measure the tissue response, and send the response along the catheter back to a hardware device.

15. The device of claim 1, wherein the at least one electrode includes one or more pairs of electrodes.

16. The device of claim 1, wherein the at least one electrode comprises one or more bipolar electrodes.

17. The device of claim 1, wherein the at least one electrode comprises one or more monopolar electrodes.

18. The device of claim 1, wherein the at least one electrode comprises at least one cylindrical electrode that extends around a circumference of the elongate member.

19. The device of claim 1, wherein the elongate member is formed of a shape memory material.

20. The device of claim 19, wherein the shape memory material is Nitinol.

* * * * *